US011583255B2

(12) United States Patent
McLaughlin (10) Patent No.: US 11,583,255 B2
(45) Date of Patent: *Feb. 21, 2023

(54) PRESET FREE IMAGING FOR ULTRASOUND DEVICE

(71) Applicant: Shenzhen Mindray Bio-Medical Electronics Co., Ltd., Shenzhen (CN)

(72) Inventor: Glen W. McLaughlin, San Carlos, CA (US)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 19 days.

This patent is subject to a terminal disclaimer.

(21) Appl. No.: 17/364,670

(22) Filed: Jun. 30, 2021

(65) Prior Publication Data

US 2021/0321989 A1   Oct. 21, 2021

Related U.S. Application Data

(63) Continuation of application No. 16/240,346, filed on Jan. 4, 2019, now Pat. No. 11,064,977.

(51) Int. Cl.
| | |
|---|---|
| *A61B 8/08* | (2006.01) |
| *G06T 5/00* | (2006.01) |
| *G06T 5/50* | (2006.01) |
| *G06T 7/00* | (2017.01) |
| *G06V 10/764* | (2022.01) |
| *G06V 10/82* | (2022.01) |
| *A61B 8/00* | (2006.01) |

(52) U.S. Cl.
CPC ............ *A61B 8/5207* (2013.01); *G06T 5/001* (2013.01); *G06T 5/50* (2013.01); *G06T 7/0002* (2013.01); *G06T 7/97* (2017.01); *G06T 2207/10132* (2013.01)

(58) Field of Classification Search
None
See application file for complete search history.

(56) References Cited

U.S. PATENT DOCUMENTS

2007/0164898 A1\* 7/2007 Pan ..................... G01S 7/52066
342/104
2012/0136253 A1\* 5/2012 Kim ........................ A61B 8/08
600/443

(Continued)

FOREIGN PATENT DOCUMENTS

CN   104519960 A  *  4/2015   ........... A61B 5/0036
CN   104519960 A       4/2015

(Continued)

*Primary Examiner* — Mohammed Rachedine
(74) *Attorney, Agent, or Firm* — Kory D. Christensen (57) ABSTRACT

Aspects of the disclosed technology provide ways to detect the object of ultrasound scanning and to automatically, load system settings and image preferences necessary to generate high quality output images. In some aspects, an ultrasound system can be configured to perform steps including receiving a selection of a first transducer, identifying a body structure or organ based on a signal received in response to an activation of the first transducer, retrieving a first set of image parameters corresponding with the body structure, and configuring the first transducer based on the first set of image parameters. Methods and machine-readable media are also provided.

21 Claims, 6 Drawing Sheets

(56) References Cited

U.S. PATENT DOCUMENTS

| | | | | |
|---|---|---|---|---|
| 2014/0343428 A1* | 11/2014 | Tanaka | ................ | G01S 15/8993 |
| | | | | 600/440 |
| 2016/0074017 A1* | 3/2016 | Lee | .................... | G01S 7/52046 |
| | | | | 600/443 |
| 2019/0196600 A1* | 6/2019 | Rothberg | ................ | G06F 3/017 |
| 2019/0374165 A1* | 12/2019 | Poole | .................... | A61B 8/469 |
| 2020/0098125 A1* | 3/2020 | Langeland | ................ | G06T 7/70 |

FOREIGN PATENT DOCUMENTS

| | | | | |
|---|---|---|---|---|
| CN | 109640830 A * | 4/2019 | ........... | A61B 6/5217 |
| WO | WO-9958043 A2 * | 11/1999 | ......... | G01S 15/8997 |
| WO | WO 9958043 A2 | 11/1999 | | |
| WO | WO-2014181902 A1 * | 11/2014 | ............... | A61B 8/14 |
| WO | WO 2014181902 A1 | 11/2014 | | |
| WO | WO-2019201726 A1 * | 10/2019 | ............. | A61B 5/107 |

* cited by examiner

PRESET FREE IMAGING FOR ULTRASOUND DEVICE

CROSS-REFERENCE TO RELATED APPLICATIONS

This application is a continuation of U.S. patent application Ser. No. 16/240,346, filed Jan. 4, 2019, for PRESET FREE IMAGING FOR ULTRASOUND DEVICE, which is incorporated herein by reference.

TECHNICAL FIELD

This disclosure relates to ultrasound imaging and in particular, for ways to automatically identifying an organ or body part being scanned and selecting optimal image parameters based on the same.

BACKGROUND OF THE INVENTION

Ultrasound imaging is a widely used for examining a wide range of materials and objects across an array of different applications. Ultrasound imaging provides an effective tool for analyzing materials and objects in a non-invasive manner. As a result, ultrasound imaging is especially common in the practice of medicine as an ailment diagnosis, treatment, and prevention tool. Specifically, because of its relatively non-invasive nature, low cost and fast response time ultrasound imaging is widely used throughout the medical industry to diagnose and prevent ailments. Further, as ultrasound imaging is based on non-ionizing radiation it does not carry the same risks as other diagnosis imaging tools, such as X-ray imaging or other types of imaging systems that use ionizing radiation.

Ultrasound imaging is accomplished by generating and directing ultrasonic sound waves into a material of interest, first in a transmit phase and subsequently in a receive phase. During the transmit phase, an ultrasonic signal is transmitted into a material of interest by applying continuous or pulsed electronic signals. During the receive phase, reflections generated by boundaries between dissimilar materials are received by receiving devices, such as transducers. The reflections are then converted to electrical signals that can then be processed to determine the locations of echo sources. The resulting data can be used to produce interior images of an object or organ of interest, e.g. by displaying images using a display device, such as a monitor.

Ultrasound imaging can offer a wealth of clinical information. Specifically, ultrasound imaging can be used in abdominal ultrasound (to visualize abdominal tissues and organs), bone sonometry (to assess bone fragility), breast ultrasound (to visualize breast tissue), doppler fetal heart rate monitors (to listen to a fetal heart beat), doppler ultrasound (to visualize blood flow through a blood vessel, organs, or other structures), echocardiogram (to view a heart), fetal ultrasound (to view a fetus in pregnancy), ultrasound-guided biopsies (to collect a sample of tissue), ophthalmic ultrasound (to visualize ocular structures) and ultrasound-guided needle placement (in blood vessels or other tissues of interest). Ultrasound imaging has also been used in describing various disease states, such as diseases of the liver, breast, prostate, thyroid or other organs through single measurements of stiffness or shear wave velocity.

Typically ultrasound systems include a main processing console and an ultrasound transducer. The ultrasound transducer can include one or more transducers (e.g., a transducer array) that is typically positioned away from the main console and controlled by a user/operator in gathering ultrasound image data.

In conventional operation, the user/operator is responsible for adjusting transducer parameters, and optimizing the image output settings to produce optimal images. Because of the numerous variables attendant in different patients with various disease states (e.g., weight, fat content, tissue density, etc.), it is difficult for manufacturers to pre-program optimal transducer parameters and image settings. Therefore, a need exists to provide a way to automatically optimize ultrasound (back-end) and image (front-end parameters) to produce optimal ultrasound images while minimizing setup time.

SUMMARY

Aspects of the disclosed technology provide an ultrasound imaging system that includes one or more processors, a plurality of transducers coupled to the one or more processors, and a non-transitory computer-readable medium coupled to the processors. The computer-readable medium includes instructions to cause the processors to perform operations including: receiving a selection of a first transducer, identifying a body structure based on a signal received in response to an activation of the first transducer, and retrieving a first set of image parameters corresponding with the body structure. In some aspects, the instructions can further cause the processors to perform operations for configuring the first transducer based on the first set of image parameters, collecting a first image from the body structure via the first transducer, using the first set of image parameters, and analyzing one or more properties of the first image to determine if any additional image parameters need to be updated.

In another aspect, the disclosed technology provides a method for optimizing ultrasound/sonogram images that includes steps for: receiving a selection of a first transducer, wherein the first transducer is positioned on a body structure, identifying the body structure, and retrieving a first set of image parameters corresponding with the body structure. In some aspects, the method can further include steps for configuring the first transducer based on the first set of image parameters, collecting a first image from the body structure via the first transducer, using the first set of image parameters, and analyzing one or more properties of the first image to determine if any additional image parameters need to be updated.

In yet another aspect, the disclosed technology provides a non-transitory computer-readable storage medium (e.g., a program product) that is configured to cause an imaging system to perform operations for receiving a selection of a first transducer, identifying a body structure based on a signal received in response to an activation of the first transducer, and retrieving a first set of image parameters corresponding with the body structure. In some aspects, the operations further include configuring the first transducer based on the first set of image parameters, collecting a first image from the body structure via the first transducer, using the first set of image parameters, and analyzing one or more properties of the first image to determine if any additional image parameters need to be updated.

DETAILED DESCRIPTION

The detailed description set forth below is intended as a description of various configurations of the subject technology and is not intended to represent the only configurations in which the subject technology can be practiced. The appended drawings are incorporated herein and constitute a part of the detailed description. The detailed description includes specific details for the purpose of providing a more thorough understanding of the subject technology. However, it will be clear and apparent that the subject technology is not limited to the specific details set forth herein and may be practiced without these details. In some instances, structures and components are shown in block diagram form in order to avoid obscuring the concepts of the subject technology.

Aspects of the disclosed technology address the aforementioned limitations of conventional ultrasound imaging systems by providing ways to automatically identify an anatomical region being scanned, and adaptively modify image system settings to obtain images aligned with the user/operator's aesthetic preferences. The automatic image optimization technology provides multiple advantages, including improved exam quality, consistency, and efficiency, as the system eliminates the need for an operator to perform time-consuming preset searching and adjustment. Eliminating the need for an operator to select image presets is not only advantageous for the system user/operator, but also provides a significant improvement for system developers. For example, a conventional high end ultrasound system typically supports around 15 to 25 transducers, each of which can have up to 50 presets and support around 5 different modes of operation. As a result, the acoustic/clinical team typically needs to optimize around 5,000 image modes, requiring the setting/tuning of several hundred parameters. Such calibrations can typically take up to one day per mode; therefore, bringing up a new system can take on the order of 20 person-years (assuming a 250 day work-year). The ability to reduce ultrasound system calibration to an automatic process not only benefits the users but also development companies, enabling them to spend more time on system development, while lowering development costs.

Aspects of the disclosed technology provide methods for automatically identifying/classifying a region of anatomy being scanned, and for automatically optimizing image preset parameters. Classification of the portions of anatomy being scanned can be performed using a machine learning (ML) classifier, such as a multilevel perceptron neural network. Once the anatomy is correctly identified, preset system parameters, such as anatomy-specific transducer presets, are automatically selected and used when generating output images. The generation of output images can be additionally informed by user/operator image preferences that can be calibrated by the user upon system initialization or startup.

In some aspects, image preferences can be learned on a user-by-user basis, for example, based on user selections and feedback that indicate their aesthetic preferences. In some embodiments, user image preferences can be determined by a process in which the user is shown a series of comparison images and prompted select those that best suit their liking. Comparison images can be provided that cover a full range of modalities and organs, as image preferences can depend on what the user is viewing, as well as what imaging modality is used. For example, basic images could be of a B-mode variety but they might vary in the type of B-mode like harmonic imaging, spatial compounding, frequency compounding and the like. A more detailed description of the processes used for identifying anatomical targets, and for optimizing output images is discussed with respect to FIGS. 2 and 3, below.

Figure 1:
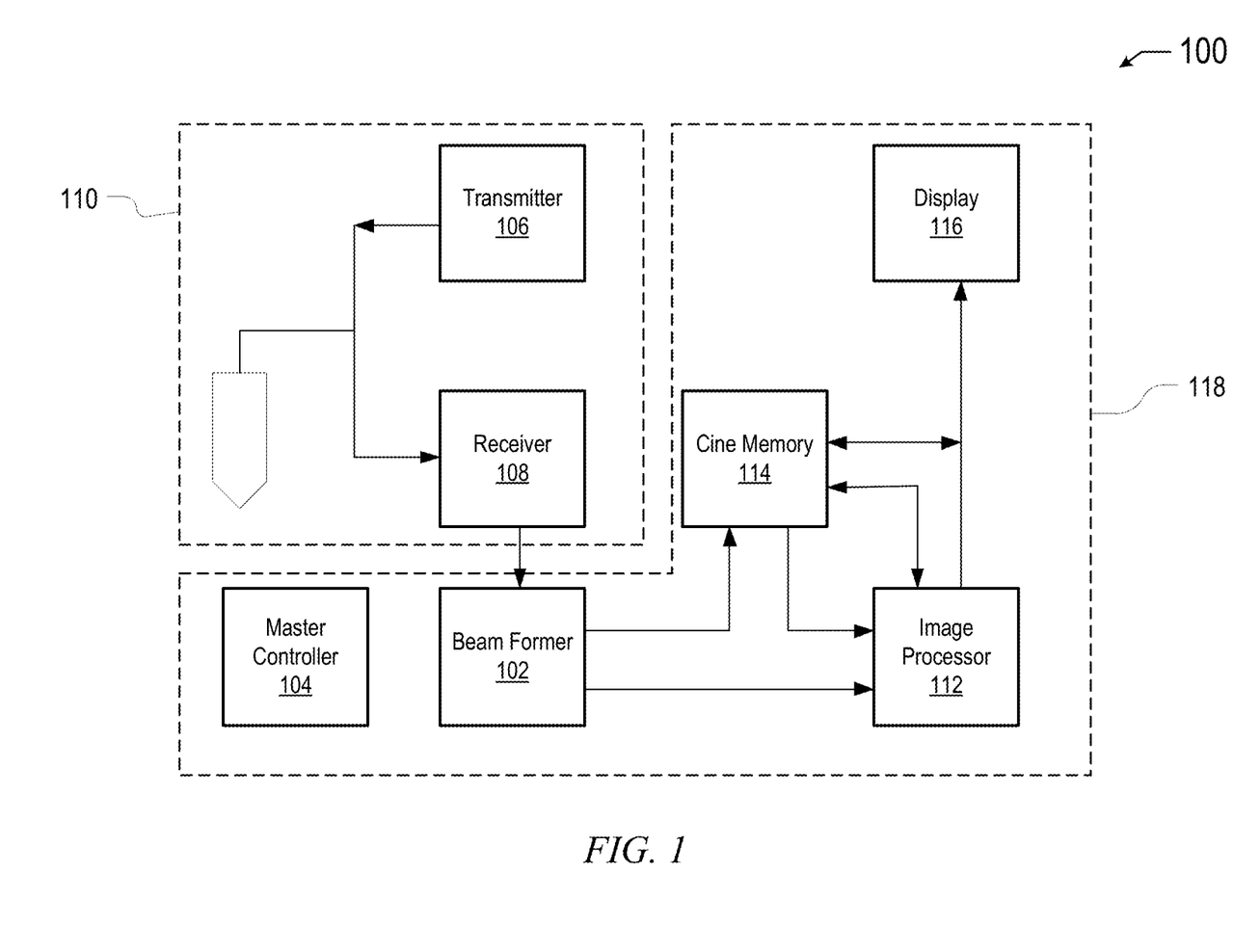
FIG. 1 illustrates an example of an ultrasound system that can be used to implement image optimization techniques of the disclosed technology.

Turning now to FIG. 1, which illustrates ultrasound system 100 in which various aspects of the disclosed technology can be implemented. Ultrasound system 100 is provided as an example system and in various embodiments, can have greater (or fewer) components than illustrated in FIG. 1. Ultrasound system 100 can be an ultrasound system where the receive array focusing unit is referred to as a beam former 102, and image formation can be performed on a scanline-by-scanline basis.

System control can be centered in the master controller 104, which accepts operator inputs through an operator interface and in turn controls various subsystems. For each scan line, transmitter 106 generates a radio-frequency (RF) excitation voltage pulse waveform and applies it with appropriate timing across the transmit aperture (defined by a sub-array of active elements) to generate a focused acoustic beam along the scan line. RF echoes received by aperture 108 of transducer 110 are amplified and filtered by receiver 108, and then fed into beam former 102, whose function is to perform dynamic receive focusing, i.e., to re-align the RF signals that originate from the same locations along various scan lines.

Image processor 112 can perform processing specific to active imaging mode(s) including 2D scan conversion that transforms the image data from an acoustic line grid to an X-Y pixel image for display. For Spectral Doppler mode, image processor 112 can perform wall filtering followed by spectral analysis of Doppler-shifted signal samples using a sliding FFT-window. Image processor 112 can also generate the stereo audio signal output corresponding to forward and reverse flow signals. In cooperation with master controller 104, image processor 112 also can format images from two or more active imaging modes, including display annotation, graphics overlays and replay of cine loops and recorded timeline data.

Cine buffer 114 provides resident digital image storage for single image or multiple image loop review, and acts as a buffer for transfer of images to digital archival devices. Video images at the end of the data processing path can be stored to the cine memory 114. In state-of-the-art systems, amplitude-detected, beam formed data may also be stored in cine memory 114. For spectral Doppler, wall-filtered, baseband Doppler I/Q data for a user-selected range gate can be stored in cine memory 114. Subsequently, display 116 can display ultrasound images created by image processor 112 and/or images using data stored in cine memory 114.

Beam former 102, master controller 104, image processor 112, cine memory 114, and display 116 can be included as part of a main processing console 118 of ultrasound system 100. In various embodiments, main processing console 118 can include more or fewer components or subsystems. Transducer 110 can be incorporated in an apparatus that is separate from the main processing console 118, in a separate apparatus that is wired or wirelessly connected to the main processing console 118. This allows for easier manipulation of ultrasound transducer 110 when performing specific ultrasound procedures on various anatomical structures of a patient. Transducer geometries can vary depending on application. By way of example, curved transducers tend to be used for abdominal and OB/GYN applications, as well as for coverage of body areas when additional penetration is needed, for example, in very large legs. Linear transducers tend to be used on more superficial structures like thyroid, vascular, and/or arterial structures, and the like. As understood by those of skill in the art, several other types of transducers may be used, such as, intraoperative, gastro scopes, trans esophageal, surgical, catheter, and the like. However, standard transducer geometries tend to fall under the categories of: curved, linear and/or face.

Figure 2:
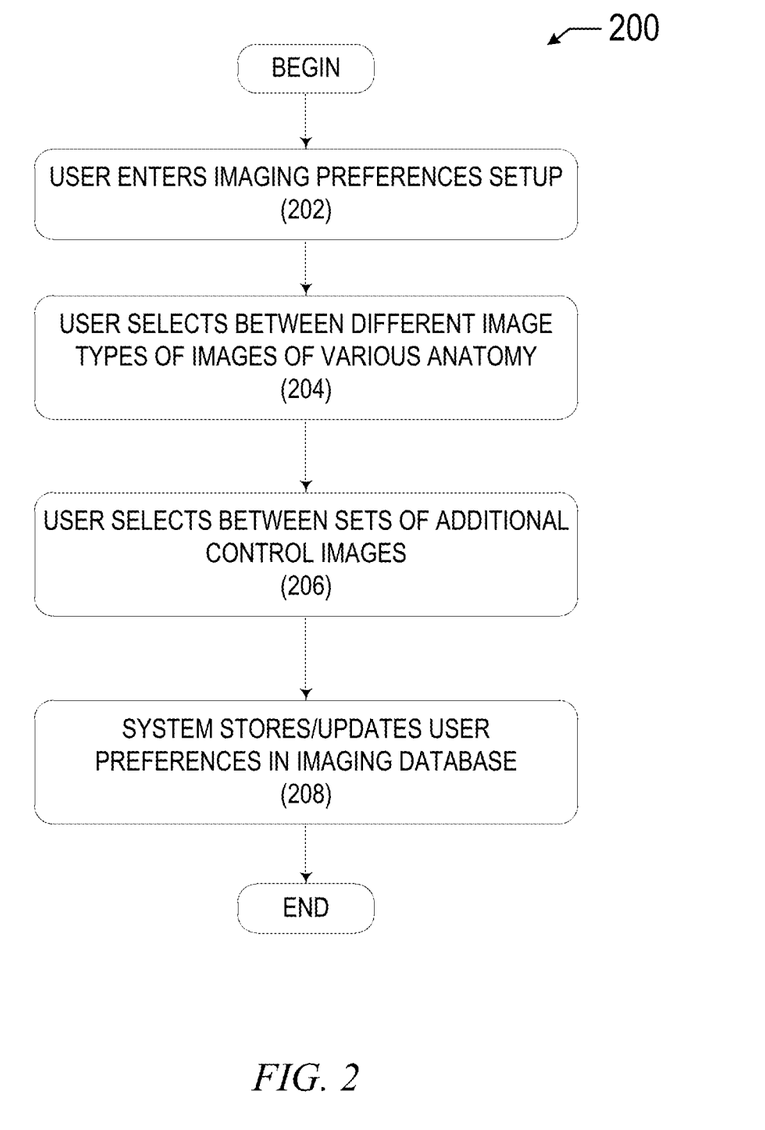
FIG. 2 illustrates steps of an example process for determining ultrasound operator imaging preferences.

FIG. 2 illustrates steps of an example process 200 for determining operator image preferences. Process 200 begins when instructions are executed to place the operator/user into an imaging preferences setup mode (202). The setup mode enables the user to manually set or configure individual image preferences, either based on a series of aesthetic choice selections, or by manually configuring system settings, such as transducer parameters. As used herein, user image preferences can be affected by backend parameters, (e.g., transducer or system data collection settings), or by front end parameters (e.g., image transformations applied after image collection). By way of example, output image aesthetics can be affected by gain, dynamic range, speckle texture, tint, color map, CD processing, CD scale, PW wall filter, tint, and the like.

Next, the user is presented with a variety images reflecting different backend and front-end parameter configurations (204). In some approaches, the user is presented with side-by-side images and prompted to select those with the greatest aesthetic appeal. As such, aesthetic preference of the user can be communicated using an A/B image comparison process for specific anatomical regions. To ensure that user preferences are adequately captured a variety of different image types are displayed to the user, so that user preferences across a variety of image modes can be inferred from the user's selections. By way of example, users can be prompted to select between various image types, including but not limited to: B-mode, CD-mode, PW-mode, M-mode, Elastography, 3D/4D, and CEUS images, etc. Different image types can also be displayed for various anatomical regions, and can represent a wide variety of image settings e.g., for dynamic range, tint, speckle texture, persistence, and map settings, etc., to ensure that the user's preferences are well captured. In some aspects, additional control images may be provided to the user for further preference learning (206). Once a user's preferences (profile) is understood by the system, basic parameters can be extracted and stored into a database (step 208) that can be used to align image collection and display strategies with those of the users preferences, as discussed in further detail below with respect to FIG. 3.

Figure 3:
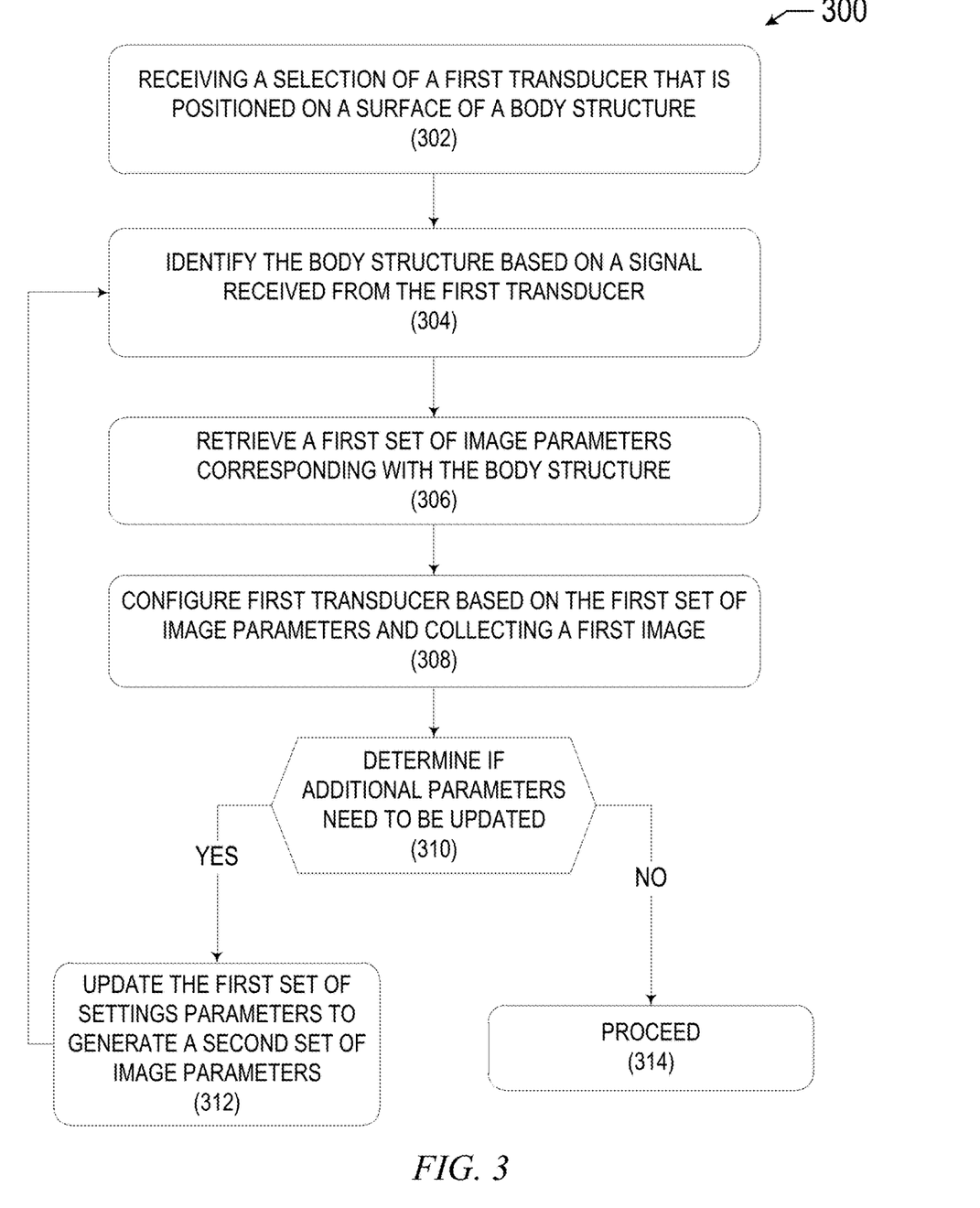
FIG. 3 is a block diagram of an example process for automatically identifying an object/organ to be scanned and loading/updating one or more corresponding imaging parameters and settings.

FIG. 3 illustrates a block diagram of an example process 300 for automatically identifying an object/organ to be imaged and loading/updating one or more corresponding image parameters and settings. Process 300 beings with the user selection of a first transducer that is positioned on a surface of a body structure, i.e., a discrete portion of anatomy to be the subject of imaging/scanning (302). Transducer selection can be communicated in a variety of ways, including, the user's selection/engagement with a particular type of transducer wand or probe apparatus. As discussed above, transducer/probe geometries can vary depending upon the type of anatomy to be scanned. In other aspects, transducer selection may be provided through user engagement with a control menu on the imaging system.

Next, the imaging system automatically identifies the body structure to be scanned based on signals received from the first transducer (step 304). As discussed in further detail below, identification/classification of the target body structure/anatomy can be performed using a machine learning classifier, such as a multilayer perceptron neural network. In alternative embodiments, anatomy identification may also be performed by comparing the scan anatomy with a database of known anatomical features or structures.

Once the body structure has been identified, one or more backend parameters, such as parameters of the first transducer, can be retrieved from a database, for example, that correlates, system configurations for performing image collection with anatomy type (306). Because different anatomical regions and have different imaging presets, the automatic identification of the anatomy to be scanned can be used to automate the preloading and configuration of system image collection and display settings, without the need for input from the user (308). After the first transducer has been configured based on settings/parameters retrieved in step 306, one or more initial images (e.g. a first image) can be collected from the target anatomy and used to determine if any additional parameters need to be updated (310).

The determination of whether or not the initially collected images achieve user's desired quality of image output can be performed using an automatic process, such as by comparing image characteristics with a database of known user preferences or previously accepted images. Alternatively, manual input provided from the user can be used to determine if additional configuration changes are needed. If it is determined in step 310 that no additional configuration changes are needed, process 300 advances to step 314 and the imaging processes is allowed to proceed.

Alternatively if it is determined in step 310 that additional image parameters need to be updated, process 300 advances to step 312 in which the first set of settings parameters are updated to generate a second set of image parameters. In such aspects, process 312 proceeds (back) to step 304, iterating the process of body structure identification and image retrieval (e.g., steps 304-310) until the image output is of adequate quality and/or indicated as acceptable by the operator/user.

Figure 4:
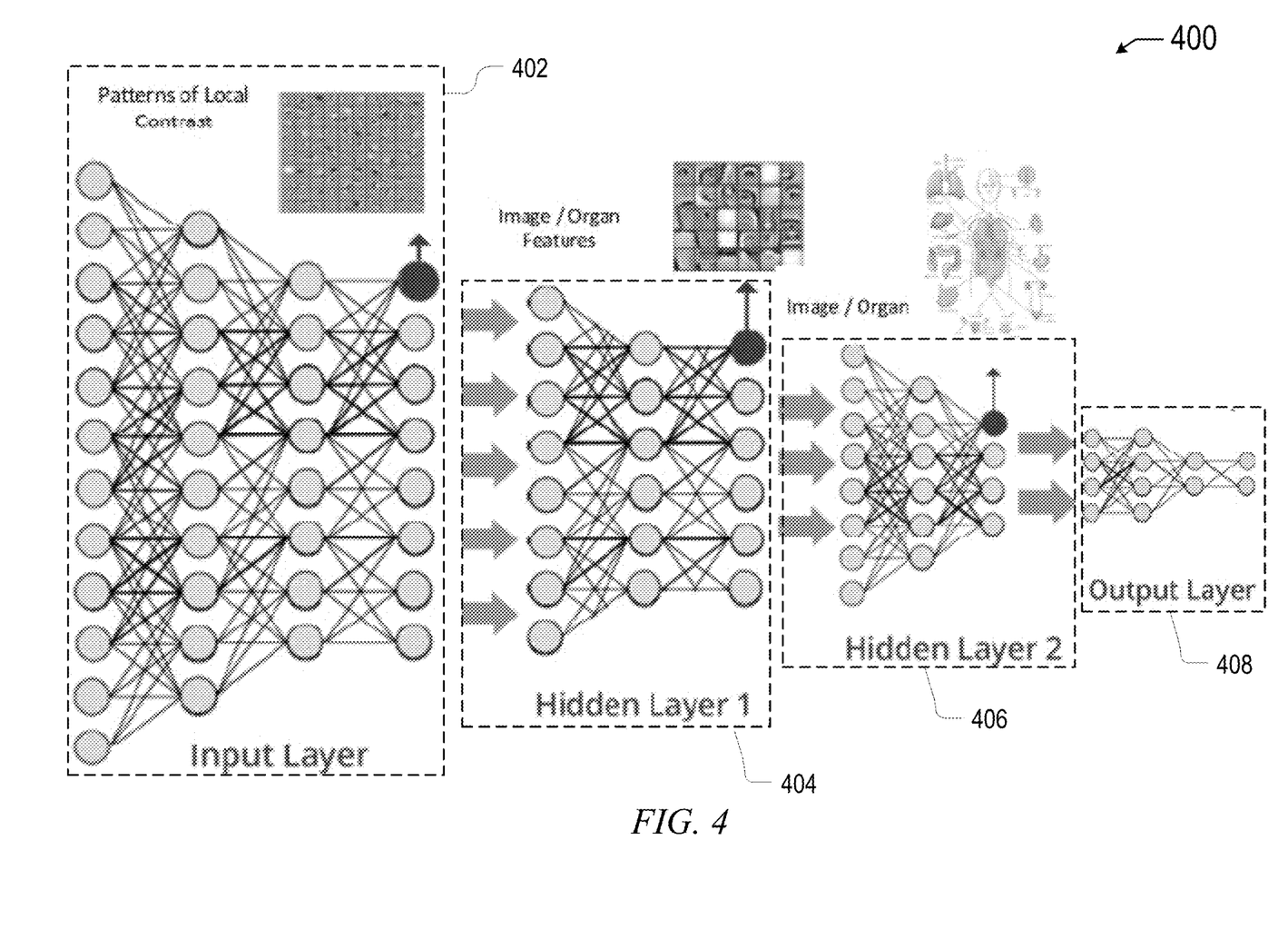
FIG. 4 conceptually illustrates various layers of a machine-learning (ML) model that can be used to automatically detect an object/organ that is being scanned.

As discussed above, anatomy identification can be performed using a machine learning classifier, such as a multilayer perceptron neural network discussed in further detail with respect to FIG. 4.

Specifically, FIG. 4 conceptually illustrates various layers of a machine-learning (ML) classifier 400 that can be used to automatically detect an object/organ being scanned, as described with respect to FIG. 3. Classifier 400 includes four total layers: an input layer 402, a first hidden layer 404, a second hidden layer 406, and an output layer 408. Those of skill in the art would understand that a greater (or fewer)

number of layers may be implemented, without departing from the scope of the technology. By way of example, a deep learning approach containing a large number of layers may be implemented.

In the illustrated example, input layer 402 is configured to receive an ultrasound image (input), and to disaggregate the input into various patterns of local contrast, which are then provided as an input to first hidden layer 404. First hidden layer 404 receives the input from input layer 402, and provides an output corresponding with the classification of specific organ features to second hidden layer 406. In turn, second hidden layer 406 provides a classification for whole organ types, with the output being provided to output layer 408, eventually resulting in an anatomy classification for the original input image provided to input layer 402. As discussed above, this classification can inform the system's retrieval of various presets, including backend settings and system parameters, and frontend image transformations.

It is understood that multilevel perceptron neural network architectures are only one example of a machine learning approach that can be implemented. In other aspects, different machine learning approaches can be used. For example, such classifiers can include, but are not limited to: a Multinomial Naive Bayes classifier, a Bernoulli Naive Bayes classifier, a Perceptron classifier, a Stochastic Gradient Descent (SGD) Classifier, and/or a Passive Aggressive Classifier, or the like. Additionally, the ML models can be configured to perform various types of regression, for example, using one or more various regression algorithms, including but not limited to: a Stochastic Gradient Descent Regressor, and/or a Passive Aggressive Regressor, etc.

Figure 5:
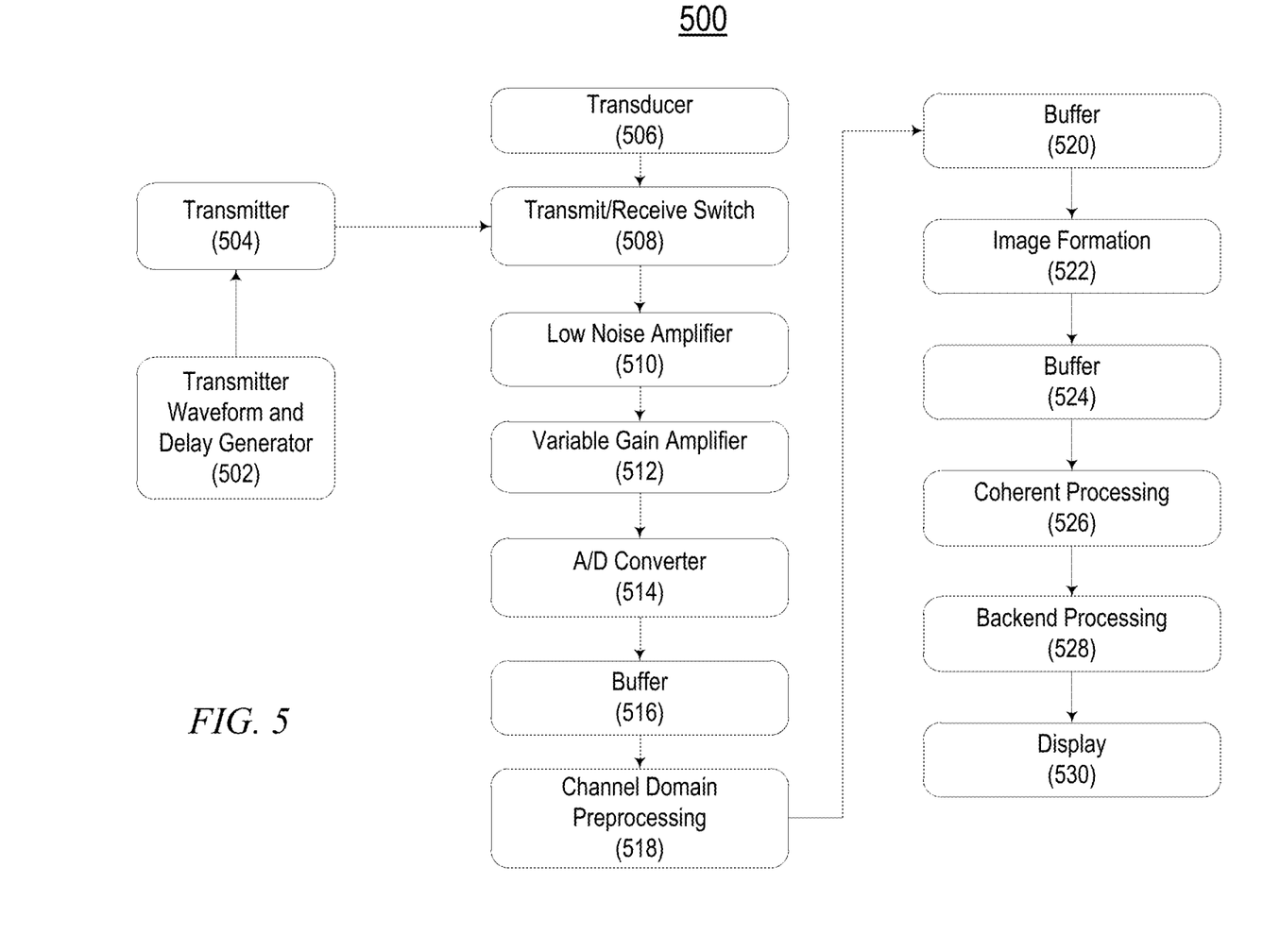
FIG. 5 illustrates an example of an image processing path that can be used to implement an ultrasound system of the disclosed technology.

FIG. 5 illustrates an example of an image processing path 500 that can be used to implement an ultrasound imaging system of the disclosed technology. It is understood that imaging path 500 represents one example processing pipeline that can be used, however, that a greater or fewer number of functional units may be deployed, depending on the desired implementation.

Processing path 500 includes a transmitter, waveform, and delay generator 502 that is configured to transmit sound waves into a body/organ being imaged. In some aspects, delay generator 502 is configured to determine an aperture, delay profile, windowing function, and power of the transmit profile. All these parameters are potential candidates for modification of the imaging system, for example, to optimize image output performance (e.g. back-end parameters, as discussed above).

The output of delay generator 502 is connected to transmitter/s 504, that receive input signals and amplifies them to levels needed to drive a transducer. The output of transmitter/s 504 is provided to transmit/receive switch 508, which is configured to allow the output of transmitter 504 to be connected to transducer 506, while preventing it from potentially destroying low-noise amplifier 510. Subsequently, waveforms are emitted from transducer 506, and received by the same transducer (506) after interacting with the organ/tissue being imaged. These receive signals pass through transmit/receive switch 508, and are amplified by low noise amplifier 510. In some implementations, low noise amplifier 510 can have several different gain settings that can be configured based on the desired imaging mode, as discussed above (e.g. as backend parameters). The output of low noise amplifier 510 is then provided to a variable gain amplifier 512. In some aspects, variable gain amplifier 512 is configured to amplify the received input signal at a rate needed to compensate for signal attenuation over time. In some implementations, the amplification rate of variable gain amplifier 512 can be configured/programmed, e.g., by a user or operator of the system. The output of variable gain amplifier 512 is then received by an analog-to-digital converter 514, for example, to convert the signal from an analog waveform to a digital waveform.

Analog-to-digital converter 514 can be configured to automatically adjust the sampling rate. The output of analog-to-digital converter 514 is then stored in buffer 516. Once the data has been stored and can be processed, it is provided to channel domain pre=processing module 518. Processing model 518 can be configured to work on single transducer element data, and to process it on a sample-by-sample basis for gain, frequency, bandwidth, and/or decoding, and the like. In some implementations, processing module 518 may also be configured to process multiple transmit/receive cycles of data, for example, for data averaging, decoding, nonlinear processing, and the like.

Post-processing, the data is then transferred to buffer 520, and routed to image formation module 522. Image formation module 522 is configured to process the received data to form an image. In some implementations, image formation module 522 can be configured to apply a variety of processing transformations, including, but not limited to a delay, a sum, a filter, gain, and various forms of adaptive processing of the above, etc. Data output from image formation block 522 is then buffered (e.g. in buffer 524) before being transferred to a coherent processing module 526.

In some implementations, coherent processing module 526 is configured to perform additional processing, for example, that can include nonlinear signal extraction, filtering for synthetic aperture processing techniques, and the like. Data entering and leaving coherent processing module 526 has both phase and magnitude information; the data from coherent processing module 526 is then passed to a backend processing module 528. Backend processing module 528 performs various forms of sampling, filtering and conversion, including but not limited to: up-sampling, down-sampling, log compression, detection, spatial filtering, adaptive filtering, scan conversion, and the like, so that the data can be displayed on a display ultimately outputted to display device 530.

It is understood that similar processing techniques can be applied to different image mode types, without departing from the disclosed technology. For example, similar steps may be applied for harmonic mode, contrast enhanced ultrasound mode, spatial compounding, frequency compounding, and the like. It is also understood that aspects of the disclosed technology are applicable to processing step or other image modes, such as, CD-mode, PW=Doppler, M-mode, color M-mode, etc.

Figure 6:
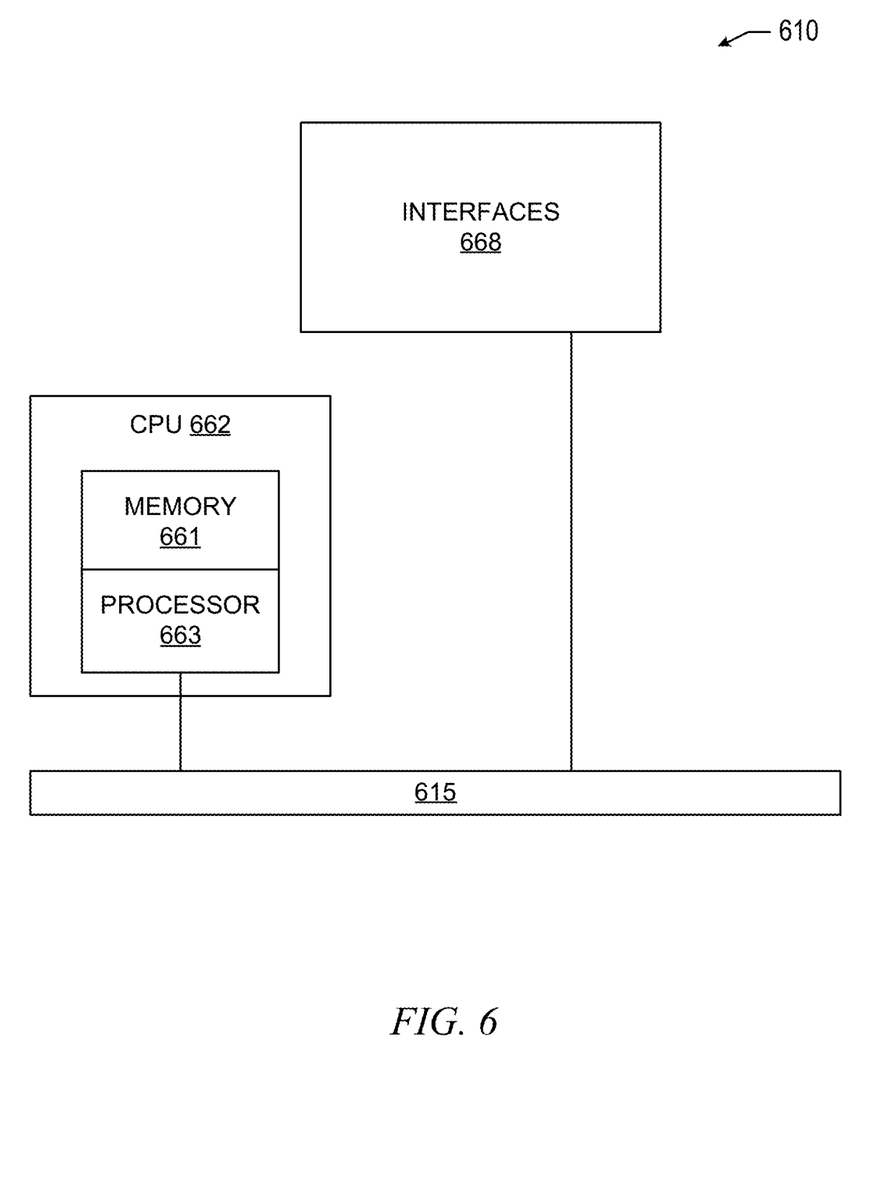
FIG. 6 is a block diagram of an example computing device that can be used to implement an automatic tissue/organ detection process, including the loading and updated of image parameters and settings, according to some aspects of the subject disclosure.

FIG. 6 is a block diagram of an example computing device that can be used to implement an automatic object/organ detection process, including the loading and update of image parameters and settings, according to some aspects of the subject disclosure. Device 610 includes central processing unit (CPU) 662, network interfaces 668, and a bus 615 (e.g., a PCI bus). When acting under the control of appropriate software or firmware, the CPU 662 is responsible for executing a method for receiving a selection of a first transducer, wherein the first transducer is positioned on a surface of a body structure, identifying the body structure based on a signal received in response to an activation of the first transducer, and retrieving a first set of image parameters corresponding with the body structure. In some aspects, CPU 662 is further configured for performing operations for configuring the first transducer based on the first set of image parameters; and collecting a first image from the body structure via the first transducer, using the first set of image parameters, analyzing one or more properties of the first image to determine if any additional image parameters need to be updated.

In some aspects, CPU 662 is further configured for performing operations for updating the first set of settings parameters to generate a second set of image parameters, if it is determined that additional image settings need to be updated, configuring the first transducer based on the second set of image parameters, collecting a second image from the body structure via the first transducer, using the second set of image parameters, and analyzing one or more properties of the second image to determine if any additional image parameters need to be updated.

CPU 662 can accomplish all these functions under the control of software including an operating system and any appropriate applications software. CPU 662 may include one or more processors 663, such as a processor from the INTEL X86 family of microprocessors. In some cases, processors 663 can be specially designed hardware for controlling the operations of image processing device 610. In some cases a computer-readable memory, e.g., memory 661 (a non-volatile Random Access Memory (RAM), or a Read Only Memory (ROM), etc., also forms part of CPU 562. However, there are many different ways in which memory could be coupled to the system.

Interfaces 668 can be provided as modular interface cards (sometimes referred to as "line cards"). They can control the sending and receiving of data packets over the network and sometimes support other peripherals used with image processing device 610. Among the interfaces that may be provided are Ethernet interfaces, frame relay interfaces, cable interfaces, Digital Subscriber Line (DSL) interfaces, token ring interfaces, and the like. In addition, various very high-speed interfaces may be provided such as fast token ring interfaces, wireless interfaces, Ethernet interfaces, Gigabit Ethernet interfaces, ATM interfaces, High Speed Serial Interfaces (HSSIs), POS interfaces, FDDI interfaces, WIFI interfaces, 3G/4G/5G cellular interfaces, CAN BUS, LoRA, and the like. Generally, these interfaces may include ports appropriate for communication with the appropriate media. In some cases, they may also include an independent processor and, in some instances, volatile RAM.

Although the system shown in FIG. 6 is one specific image processing device of the disclosed embodiments, it is by no means the only device architecture on which aspects of the disclosed technology can be implemented. For example, an architecture having a single processor that handles communications as well as routing computations, etc., is often used. Further, other types of interfaces and media could also be used with image processing device 610.

Regardless of the image processing device's configuration, it may employ one or more memories or memory modules (including memory 661) configured to store program instructions for the general-purpose network operations and mechanisms for roaming, route optimization and routing functions described herein. The program instructions may control the operation of an operating system and/or one or more applications, for example.

Image processing device 610 can also include an application-specific integrated circuit (ASIC), which can be configured to perform any of the operations described above. The ASIC can communicate with other components in the image processing device 610 via bus 615, to exchange data and signals and coordinate various types of operations by image processing device 610.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from non-transitory forms of computer-readable media. Such instructions can comprise, for example, instructions and data which cause or otherwise configure a general purpose computer, special purpose computer, or special purpose processing device to perform a certain function or group of functions.

Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example. The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

The foregoing description has been directed to specific embodiments. It will be apparent, however, that other variations and modifications may be made to the described embodiments, with the attainment of some or all of their advantages. For instance, it is expressly contemplated that the components, elements, and/or operations described herein can be implemented as software being stored on a tangible (non-transitory) computer-readable medium, devices, and memories (e.g., disks/CDs/RAM/EEPROM, etc.) having program instructions executing on a computer, hardware, firmware, or a combination thereof. Further, methods describing the various functions and techniques described herein can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network.

The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on. In addition, devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example. Instructions, media for conveying such instructions, computing resources for executing them, and other structures for supporting such computing resources are means for providing the functions described in these disclosures. Accordingly this description is to be taken only by way of example and not to otherwise limit the scope of the embodiments herein. Therefore, it is the object of the appended claims to cover all such variations and modifications as come within the true spirit and scope of the embodiments herein.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

Additionally, it is understood that any specific order or hierarchy of steps in the processes disclosed is an illustration of exemplary approaches. Based upon design preferences, it is understood that the specific order or hierarchy of steps in the processes may be rearranged, or that only a portion of the illustrated steps be performed. Some of the steps may be performed simultaneously. For example, in certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more."

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A phrase such as a configuration may refer to one or more configurations and vice versa.

The word "exemplary" is used herein to mean "serving as an example or illustration." Any aspect or design described herein as "exemplary" is not necessarily to be construed as preferred or advantageous over other aspects or designs. Those having skill in the art will appreciate that many changes may be made to the details of the above-described embodiments without departing from the underlying principles of the invention. The scope of the present invention should, therefore, be determined only by the following claims.

What is claimed is:

1. An ultrasound imaging system, comprising:
an ultrasound transducer; and
a processor coupled to the ultrasound transducer, wherein the processor is configured to:
  automatically identify, using a machine learning (ML) classifier, an anatomical structure within a patient's body based on a signal received from the ultrasound transducer;
  retrieve, from a computer-readable storage medium, a first set of transducer parameters corresponding to the anatomical structure;
  configure the ultrasound transducer based on the first set of transducer parameters; and
  collect a first image of the anatomical structure via the ultrasound transducer using the first set of transducer parameters.

2. The ultrasound imaging system of claim 1, wherein the processor is further configured to:
  determine whether the first image meets a desired image quality;
  if the first image does not meet the desired image quality, update the first set of transducer parameters to generate a second set of transducer parameters;
  configure the ultrasound transducer based on the second set of transducer parameters; and
  collect a second image of the anatomical structure via the ultrasound transducer, using the second set of transducer parameters.

3. The ultrasound imaging system of claim 2, wherein the processor automatically determines whether the first image meets the desired image quality based on image characteristics of the first image.

4. The ultrasound imaging system of claim 3, wherein the processor automatically determines whether the first image meets a desired image quality by comparing the image characteristics with a database of known user preferences or image characteristics of images previously accepted by a user.

5. The ultrasound imaging system of claim 2, wherein the processor determines whether the first image meets the desired image quality based on manual input from a user whether the first image is accepted.

6. The ultrasound imaging system of claim 1, wherein the first set of transducer parameters are previously provided by a user for the anatomical structure.

7. The ultrasound imaging system of claim 6, wherein the first set of transducer parameters are previously provided by the user for the anatomical structure in response to an A/B comparison based on images generated by different image parameters.

8. The ultrasound imaging system of claim 2, wherein the processor is configured to update the first set of transducer parameters based on user input.

9. The ultrasound imaging system of claim 8, wherein the processor is further configured to update the ML classifier based on the user input.

10. The ultrasound imaging system of claim 8, wherein at least one parameter of the first set of transducer parameters comprises an aperture, a delay profile, a windowing function, or a power of a transmit profile.

11. The ultrasound imaging system of claim 8, wherein the ML classifier comprises a multilayer perceptron neural network.

12. A computer-implemented method for optimizing sonogram images, comprising:
    automatically identifying, using a machine learning (ML) classifier, an anatomical structure within a patient's body based on a signal received from an ultrasound transducer;
    retrieving, from a computer-readable storage medium, a first set of transducer parameters corresponding to the anatomical structure;
    configuring the ultrasound transducer based on the first set of transducer parameters; and
    collecting a first image of the anatomical structure via the ultrasound transducer using the first set of transducer parameters.

13. The computer-implemented method of claim 12, further comprising:
    determining whether the first image meets a desired image quality;
    if the first image does not meet the desired image quality, updating the first set of transducer parameters to generate a second set of transducer parameters;
    configuring the ultrasound transducer based on the second set of transducer parameters; and
    collecting a second image of the anatomical structure via the ultrasound transducer, using the second set of transducer parameters.

14. The computer-implemented method of claim 13, wherein determining whether the first image meets the desired image quality comprises determining whether the first image meets the desired image quality based on image characteristics of the first image.

15. The computer-implemented method of claim 14, wherein determining whether the first image meets the desired image quality comprises comparing the image characteristics with a database of known user preferences or image characteristics of images previously accepted by a user.

16. The computer-implemented method of claim 13, wherein determining whether the first image meets the desired image quality comprises receiving manual input from a user as to whether the first image is accepted.

17. The computer-implemented method of claim 13, wherein the first set of transducer parameters are previously specified by a user for the anatomical structure or determined in response to an A/B comparison by the user based on images generated by different image parameters.

18. The computer-implemented method of claim 13, wherein updating the first set of transducer parameters comprises updating the first set of transducer parameters and the ML classifier based on user input.

19. The computer-implemented method of claim 12, wherein at least one transducer parameter of the first set of transducer parameters comprises an aperture, a delay profile, a windowing function, or a power of a transmit profile.

20. The computer-implemented method of claim 12, wherein the ML classifier comprises a multilayer perceptron neural network.

21. A non-transitory computer-readable storage medium comprising instructions stored therein, which when executed by a processor, causes the processor to perform operations comprising:
    automatically identifying, using a machine learning (ML) classifier, an anatomical structure within a patient's body based on a signal received from an ultrasound transducer;
    retrieving, from a computer-readable storage medium, a first set of transducer parameters corresponding to the anatomical structure;
    configuring the ultrasound transducer based on the first set of transducer parameters; and
    collecting a first image of the anatomical structure via the ultrasound transducer using the first set of transducer parameters.

* * * * *